United States Patent
Anderlei et al.

(10) Patent No.: US 11,680,238 B2
(45) Date of Patent: Jun. 20, 2023

(54) METHOD FOR GASSING BIOREACTORS AND GASSING SYSTEM

(71) Applicant: ADOLF KÜHNER AG, Birsfelden (CH)

(72) Inventors: Tibor Anderlei, Müllheim (DE); Simon Paul Zumbrunnen, Oberburg (CH); Manfred Schär, Burgdorf (CH); Andreas Richter, Pratteln (CH)

(73) Assignee: ADOLF KÜHNER AG, Birsfelden (CH)

( * ) Notice: Subject to any disclaimer, the term of this patent is extended or adjusted under 35 U.S.C. 154(b) by 240 days.

(21) Appl. No.: 16/973,168

(22) PCT Filed: May 9, 2019

(86) PCT No.: PCT/EP2019/061936
§ 371 (c)(1),
(2) Date: Dec. 8, 2020

(87) PCT Pub. No.: WO2019/238320
PCT Pub. Date: Dec. 19, 2019

(65) Prior Publication Data
US 2021/0253989 A1    Aug. 19, 2021

(30) Foreign Application Priority Data
Jun. 15, 2018 (DE) ..................... 10 2018 114 414.8

(51) Int. Cl.
C12M 1/00    (2006.01)
C12M 3/06    (2006.01)

(52) U.S. Cl.
CPC ............ *C12M 23/40* (2013.01); *C12M 23/58* (2013.01); *C12M 27/16* (2013.01); *C12M 23/22* (2013.01); *C12M 29/04* (2013.01); *C12M 29/20* (2013.01)

(58) Field of Classification Search
None
See application file for complete search history.

(56) References Cited

U.S. PATENT DOCUMENTS 10,138,450 B2    11/2018    Nozaki

FOREIGN PATENT DOCUMENTS

| DE | 102004023053 A1 | 12/2005 |
|----|----|----|
| EP | 0965632 A1 | 12/1999 |

(Continued)

OTHER PUBLICATIONS

Akgun et al. "Application of an improved continuous parallel shaken bioreactor system for three microbial model systems." Bioprocess Biosyst Eng (2008) 31:193-205. (Year: 2008).*

(Continued)

*Primary Examiner* — William H. Beisner
(74) *Attorney, Agent, or Firm* — Lucas & Mercanti, LLP

(57) ABSTRACT

A method, and also a gas supply system without a separate humidifying apparatus, for supplying gas to a plurality of bioreactors, divides a constant gas stream with high distribution accuracy into a plurality of gas substreams having a mandated volume flow, which can be kept constant at the mandated level even when during gas supply there is fluctuation in the opposing pressure in the gas line to the respective bioreactor, and decouples a gas distribution from the opposing pressure by hydrostatic pressure compensation, with the gas distribution at the same time producing an obligatory humidification of the gas stream.

17 Claims, 4 Drawing Sheets

(56) References Cited

FOREIGN PATENT DOCUMENTS

EP          2975110  A1    1/2016
WO     2007116266  A1   10/2007

OTHER PUBLICATIONS

Notification of Transmittal of Translation of the International Preliminary Report on Patentability, dated Dec. 15, 2020, 8 Pages.
Catalog Fa. HiTec Zang GmbH "Bioprozessoptimierung in Schüttelkolben RAMOS®—Respiration Activity Monitoring System".
Catalog Fa. Eppendorf AG "Accurate and Safe DASGIP® MX und MF4 für massendurchflussgeregelte Begasung", 2015.

* cited by examiner

METHOD FOR GASSING BIOREACTORS AND GASSING SYSTEM

CROSS-REFERENCE TO RELATED APPLICATIONS

This application is a 371 of PCT/EP2019/061936, filed May 9, 2019, which in turn claims the priority of DE 10 2018 114 414.8 filed Jun. 15, 2018. The priority of both applications is hereby claimed and both applications are incorporated herein by reference.

BACKGROUND OF THE INVENTION

The invention relates to a method for supplying gas to a plurality of bioreactors, and also to a gas supply system for carrying out the method.

A controlled supply of various gases or gas mixtures is necessary especially in the case of the automated capture of operational parameters of microbial, biochemical, enzymatic, and chemical reactions in reaction liquids in bioreactors, which may be shaken continuously in all of the microreactors up to the end of the reaction. Parameters of the reaction liquids that are captured are, for example, the oxygen transfer rate (OTR) and the carbon dioxide transfer rate (CTR), and from these the parameters of respiration quotient (RQ) and maximum specific growth rate ($\mu_{max}$) are derived.

Known from the prior art is a universal measuring system for bioprocess optimization in shake flasks through determination of the aforementioned operational parameters (cf. Hitec-Zang, Bioprozessoptimierung in Schüdttelkolben [Bioprocess optimization in shake flasks], downloaded on May 16, 2018 from https://www.hitec-zang.de/fileadmin/informationsmaterial/flyer_deu/web/RAMOS_Flyer_2013_web.pdf).

The universal measuring system has the capacity to carry out parallel tests in eight bioreactors and to capture respiration activities. For the consistent supply of gas to the culture liquids in the bioreactors, a constant gas stream is distributed over a plurality of gas lines, which are connected to a gas inlet on each bioreactor. In order to supply the eight volumetric flasks with consistent gas substreams, a local flow resistance is employed in the form of orifice plates, which produce a sudden narrowing in the line cross section. Uniform distribution of the gas requires a relatively high pressure drop of >200 mbar across the orifice plates. This relatively high pressure drop across the orifice plates ensures that small pressure losses due to differences in the length of the gas lines to the bioreactors and/or at offgas filters have virtually no effect on the uniform distribution of the gas over all of the bioreactors.

The known method for supplying gas uniformly to a plurality of bioreactors necessitates relatively high pressures in the gas provision and also relatively exacting safety measures in the use of humidification bottles for the gas, which must be rated to the higher pressures.

Furthermore, the company Eppendorf from Hamburg offers, under the designation DASGIP MX4/4, a gas mixing module which provisions four separate bioreactors with independently compiled mixtures of air, nitrogen, oxygen, and carbon dioxide. Each gas outlet has its own setpoint values for the flow rate and for the $O_2$ and $CO_2$ concentrations. The Eppendorf gas mixing module requires the use of valves and a complex electronic control system. Humidification of the gas stream requires a separate humidifying section for each of the four bioreactors (cf. Eppendorf, DASGIP® MX-Module für massendurchflussgeregeltes Gasmischen [DASGIP® MX modules for mass flow-regulated gas mixing], downloaded on May 16, 2018 from https://online-shop.eppendorf.de/DE-de/Bioprozesstechnik-44559/Module-77460/DASGIP-MX-Module-fuer-massen-durchflussgeregeltes-Gasmischen-PF-60977.html?_ga=2.18935403.1365824566.1526488598-1728287905.1526488598).

WO 2007/116266 A1 discloses a method for supplying a plurality of bioreactors with a constant gas stream from a compressed air source. The gas stream passes first through a humidification bottle and is subsequently divided by a plurality of T-pieces in a feed line into gas substreams, which are introduced, via gas lines branching off from the T-pieces, into one each of the bioreactors. In order to create substantially the same gas supply conditions in each bioreactor, means to produce opposing pressure, such as flow-regulating valves or nozzles, are proposed, situated before or after each bioreactor, with each of these means producing an opposing pressure which is greater than the resistance of the gas stream between the means generating opposing pressure.

BRIEF SUMMARY OF THE INVENTION

Proceeding from this prior art, the object on which the invention is based is that of creating a method for supplying gas to a plurality of bioreactors, and also a gas supply system, which without a separate humidification apparatus divides a constant gas stream with high distribution accuracy into a plurality of gas substreams having a mandated volume flow which can be kept constant at the mandated level even in the event of fluctuations, during gas supply, in the opposing pressure in the gas line to the respective bioreactor.

The object on which the invention is based is more particularly that of dividing a constant gas stream into a plurality of gas substreams with consistent volume flow, largely independently of the opposing pressure in the gas lines to the individual bioreactors.

The achievement of this object is based on the concept of decoupling the gas distribution from the opposing pressure by means of hydrostatic pressure compensation, with the gas distribution at the same time producing an obligatory humidification of the gas stream.

Advantageous embodiments of the invention are apparent from the dependent claims.

The division of the gas stream into a plurality of gas substreams and the introduction of each gas substream into the liquid charge cause obligatory humidification of the gas.

Each gas substream may in each case be introduced into the liquid charge below one of the riser lines. In that case each gas substream is introduced into one of the separate riser lines, having a lower opening, preferably by means of a distributor which is arranged below the riser lines and from which the individual gas substreams immerge in the form of gas bubbles and ascend in the riser lines. The distributor is fed with the gas stream via a feed line.

Alternatively, each gas substream may be introduced into the liquid charge within one of the riser lines. In that case each gas substream is introduced into one of the separate riser lines, having a lower opening, preferably by means of a distributor whose outlet openings for the gas substreams open out within the riser lines. The individual gas substreams immerge from the outlet openings in the form of gas bubbles and ascend within the liquid charge in the riser lines. The distributor is fed with the gas stream via a supply line.

In accordance with Pascal's law, the gas distribution is decoupled from the opposing pressure by hydrostatic pressure compensation as follows:

$$p(h) = \rho g h + p_0$$

where:
- $p(h)$ = hydrostatic pressure as a function of the height h of the liquid level within the riser line
- $\rho$ = density of the liquid
- $g$ = acceleration due to gravity
- $h$ = liquid level within the riser line above the lower opening of the riser line
- $p_0$ = pressure on the liquid surface in the riser line If, for example, the pressure in a gas line increases due to a blocked offgas filter on the bioreactor, there is an increase in the pressure $p_0$ on the liquid surface in the riser line affected. The rising pressure on the liquid surface has the effect that the liquid level in the riser line connected to the gas line falls relative to the liquid level in the container. The rising pressure $p_0$ on the liquid surface is compensated, according to Pascal's law, by the lower height h of the liquid level over the lower opening of the riser line. The pressure of the gas substream on the distributor, however, remains constant and enters the riser line against an unchanged hydrostatic pressure with unchanged volume flow.

Another advantage of the invention is that an increased pressure $p_0$ on the liquid surface in one of the riser lines, owing to a blocked offgas filter, for example, has no effect on the supply of gas to the remaining bioreactors.

In one advantageous embodiment of the invention, the constant gas stream is divided by means of the distributor into gas substreams with consistent volume flow. Irrespective of the opposing pressure in the gas lines connected to the riser lines, all of the bioreactors are supplied with gas with consistent volume flow, on account of the hydrostatic pressure compensation.

Where the gas substreams are introduced into the liquid charge below the riser lines, the distributor is preferably arranged at a low distance below the riser lines in a manner such that the gas substrates emerging from the distributor are introduced completely or near-completely into the riser lines, in particular even when the bioreactors are shaken.

The gas substreams are preferably introduced into the riser lines in consistent vertical distance to the liquid level. If, moreover, the gas substreams are introduced into the liquid charge in consistent vertical distance to the liquid level, the gas substreams are introduced under consistent conditions in all of the riser lines. All of the gas substreams travel a consistent path length until entry into the respective riser line and/or within the riser lines. Where the gas substreams emerging from the distributor have a consistent volume flow, there is also a consistent volume flow entering each riser line.

The method of the invention is suitable especially for supplying gas to a plurality of shaken bioreactors, since not only the bioreactors but also the container can be shaken without problems, for the humidification and distribution of the gas stream, by virtue of the exclusively mechanical components.

Key components of the gas supply system of the invention are the container, the riser lines, and the distributor connected to the feed line. The container is open on its top side and has the form, for example, of a bottle. The container contains the liquid charge into which the feed line and also the riser lines immerge, with the distributor being attached in a fluid-conducting manner at the end of the feed line. By way of the gas provision, a constant gas stream is provided in the feed line, with the gas stream able to comprise only one gas, such as oxygen, carbon dioxide, nitrogen, for example, or a gas mixture, of the aforementioned gases, for example, or sterile-filtered ambient air.

Where the gas stream comprises a gas mixture, the gas provision has a gas mixing system whose entries are connected to a plurality of gas sources for the various gases, and whose exit is connected to the feed line to the distributor. In order to keep constant the mixing ratio of the individual gases, the gas mixing system preferably has a mass flow controller (MFC) for each gas source. With the mass flow controller, the volume flow of each gas is controlled to a setpoint value. The mass flow controller typically comprises a mass flow meter, a controller which is programmable via an interface, and a proportioning valve. The required calibration data for each gas are loaded via the programming interface.

The feed lines and the riser lines of the gas supply system of the invention are implemented for stability reasons, at least in sections within the container, as tube lines which extend into the liquid charge perpendicularly to its liquid level. The perpendicular arrangement is space-saving and constructionally advantageous, especially if the riser lines are arranged circularly around the feed line. The circular arrangement of the riser tubes eliminates the effect of the shaking movement of a rotary shaker on the gas distribution in the liquid in the container, where the latter is also shaken during the supply of gas.

In one embodiment, the gas stream is distributed over the gas substreams with a plurality of distributor tubes which extend outwardly in star shape. For gas quantity restriction, the distributor tubes may have a reduced diameter (capillary tubes) or may have tapering at the end. Gas quantity restriction evens out the gas substreams. The angle between the distributor tubes corresponds to the angle between the riser lines arranged circularly around the feed line.

In a further embodiment, the distributor has a hollow-cylindrical gas collector which is in fluid communication with the feed line and at whose upper end face there are arranged a plurality of orifice plates. Each orifice plate is aligned with a lower opening of one of the riser lines. The orifice plates in the gas distributor form a flow resistance and hence serve as gas quantity restrictors for evening out the gas substreams exiting the distributor.

If the longitudinal central axes of the feed line and of the hollow-cylindrical gas collector are coincident, all of the orifice plates are geometrically consistent and are arranged at the same radial distance from the longitudinal central axis, then the flow conditions at all of the orifice plates are consistent in technical terms. The consistent flow conditions contribute to consistent gas substreams exiting at all of the orifice plates.

In order to avoid adjustment and alignment of the distributor, arranged on the feed line, in relation to the riser lines, the container in one advantageous embodiment of the invention has an opening which can be closed with a cover, with the feed line—with the distributor—and the riser lines being mounted on the cover. The aforesaid components can be handled easily as an assembly. The feed line with the distributor, and the riser lines, can be correctly positioned within the liquid charge by closing the container opening with the cover. For hydrostatic pressure compensation it is not necessary for the cover to close the container in a gastight manner. In order to prevent a sharp pressure rise in the container, it is possible, in the case of a cover that does close the container in a gastight manner, to provide a pressure relief valve or gas filter on the cover or the container.

The section of the feed line that is mounted on the cover, and the riser lines, are preferably implemented as tube lines. The gas line is connected in a gastight manner to the upper opening of each riser line, and is in fluid communication with an interior of one of the bioreactors. In order to prevent a high pressure within the bioreactors, each bioreactor preferably has a pressure relief valve and/or an offgas filter, via which pressure compensation can take place.

The container and/or the riser lines consist preferably at least partly of transparent material, more particularly of glass or plastic. The transparent material permits a visual check on the opposing pressure prevailing in the riser lines, through the visibility of the liquid level of the column of liquid in each riser line.

BRIEF DESCRIPTION OF THE DRAWINGS

The invention is illustrated below by means of the drawings, in which.

DETAILED DESCRIPTION OF THE PREFERRED EMBODIMENTS

Figure 1:
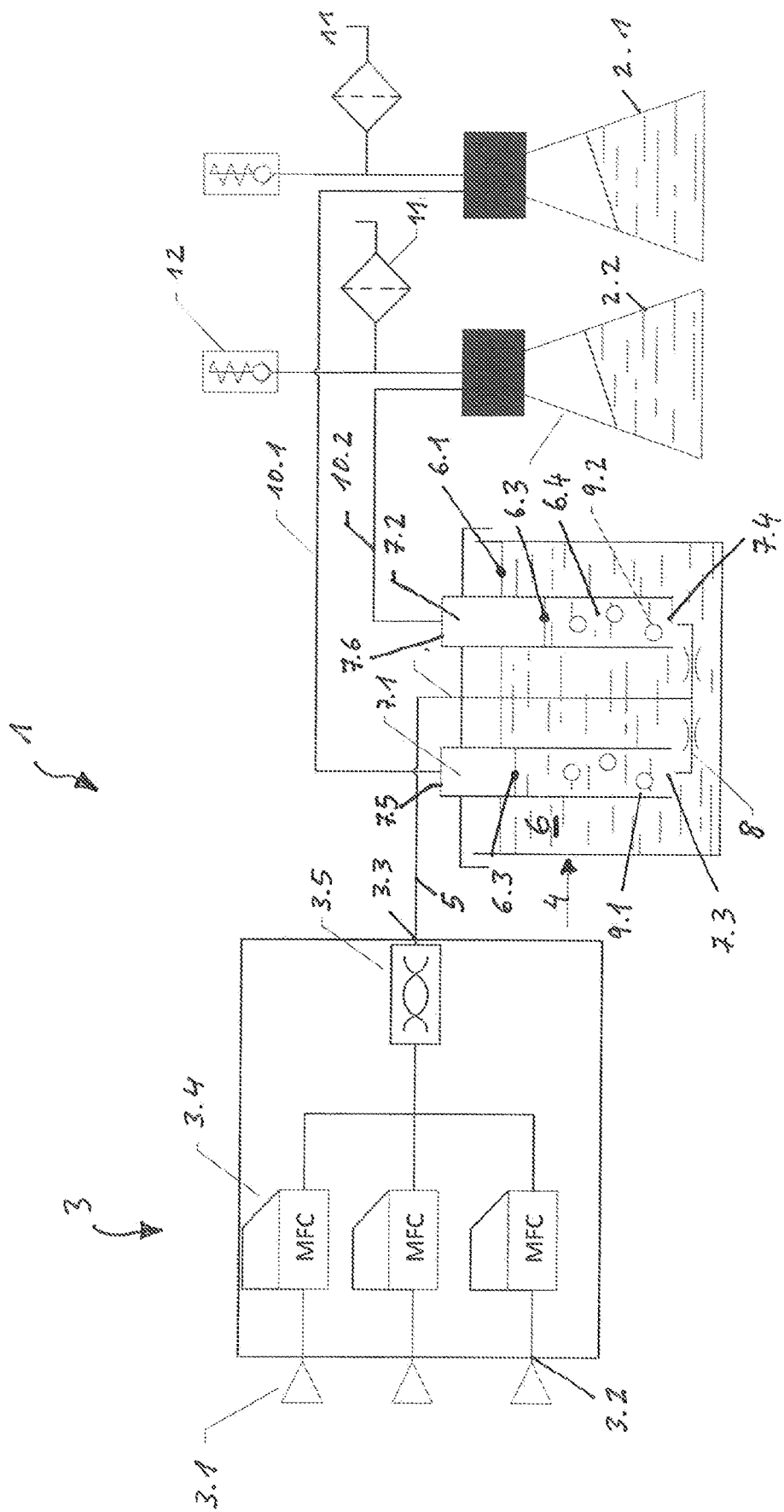
FIG. 1 shows a schematic representation of a gas supply system of the invention for supplying gas to a plurality of bioreactors.

FIG. 1 shows a scheme of a gas supply system (1) for supplying gas to a plurality of bioreactors (2.1, 2.2). In the exemplary embodiment, for reasons of clarity, only two bioreactors are shown. With the gas supply system of the invention, however, it is easily possible for more than two, for example, six, bioreactors to be supplied with gas simultaneously. The bioreactors (2.1, 2.2) are configured to receive a biomass, a liquid nutrient medium, and for introduction of the gas supply.

Further key components of the gas supply system (1) include a gas provision (3) to provide a constant gas stream, which in the exemplary embodiment comprises a mixture of three gases, and a container (4), configured to humidify and divide the gas stream into a plurality of gas substreams.

The container (4) contains a liquid charge (6), into which riser lines (7.1, 7.2) immerge perpendicularly to the liquid level (6.1). The riser lines (7.1, 7.2) are implemented as tubes, for reasons of stability, and have a consistent length and also a consistent diameter. A lower opening (7.3, 7.4) of each riser line (7.1, 7.2) is arranged above a distributor (8) which is connected in a fluid-conducting manner to the gas provision (3) via a feed line (5). The distributor (8) divides the gas stream into a number of gas substreams (9.1, 9.2), symbolized by air bubbles in FIG. 1, the number of substreams corresponding to the number of the bioreactors (2.1, 2.2).

The distributor (8) is arranged at a small distance below the lower openings (7.3, 7.4) of the riser lines (7.1, 7.2). The outlet openings of the distributor (8), however, may also open out in to the riser lines, provided it is ensured that the gas substreams are always introduced into the liquid charge (6). Connected in gastight manner to an upper opening (7.5, 7.6) of each riser line (7.1, 7.2) is a gas line (10.1. 10.2), which in each case connects one of the riser lines (7.1, 7.2) to the interior of one of the bioreactors (2.1, 2.2).

From the schematic representation it is apparent that the gas line (10.1) to the bioreactor (2.1) is longer than the gas line (10.2) to the bioreactor (2.2). Accordingly, the gas line (10.1) presents a greater flow resistance to the gas substream than does the gas line (10.2). The higher flow resistance leads to a higher pressure in the gas line (10.2) than in the gas line (10.1). The difference in gas pressure affects the liquid surface (6.3) of the column (6.4) of liquid in the riser lines (7.1, 7.2). Owing to the higher pressure in the gas line (10.2), the liquid level of the column (6.4) of liquid in the riser line (7.2) drops to a greater extent than the liquid level of the column (6.4) of liquid in the riser line (7.1).

The higher pressure acting on the liquid surface (6.3) in the riser line (7.2) is compensated by the lower height (6.5) of the column (6.4) of liquid in the riser line (7.2), and so the hydrostatic pressure effective in the two riser lines (7.1, 7.2) is substantially consistent despite the different pressures in the gas lines (10.1, 10.2).

The gas substreams (9.1, 9.2) exit the distributor (8), unaffected by the flow resistances in the gas lines (10.1, 10.2), with consistent volume flow, and enter into the columns of liquid in the riser lines (7.1, 7.2). Because of the consistent hydrostatic pressure in the riser lines (7.1, 7.2), a uniform supply of gas to the two bioreactors is ensured. Even if, for example, a gas filter (11) arranged for pressure compensation on one of the bioreactors (2.1, 2.2) were to become blocked, the consequent increase in pressure in the gas line (10.1, 10.2) would have no effect on the volume flow of the gas fed to the bioreactor (2.1, 2.2).

In the exemplary embodiment shown, the cell cultures are to be supplied with consistent gas substreams (9.1, 9.2) of a gas mixture. For this purpose, the gas provision (3) has a gas mixing system whose entries (3.2) are connected to a plurality of gas sources (3.1) and whose exit (3.3) is connected to the feed line (5). The gas sources (3.1) comprise, for example, pressurized gas bottles for oxygen, carbon dioxide, and nitrogen. For each gas source (3.1), the gas mixing system has a mass flow controller (3.4), which controls the volume flow of the gas to a setpoint value. After having been controlled to the setpoint value, the gases for mixing are fed to a mixing facility (3.5), in which the volume flows of oxygen, carbon dioxide, and nitrogen are mixed.

Figure 2:
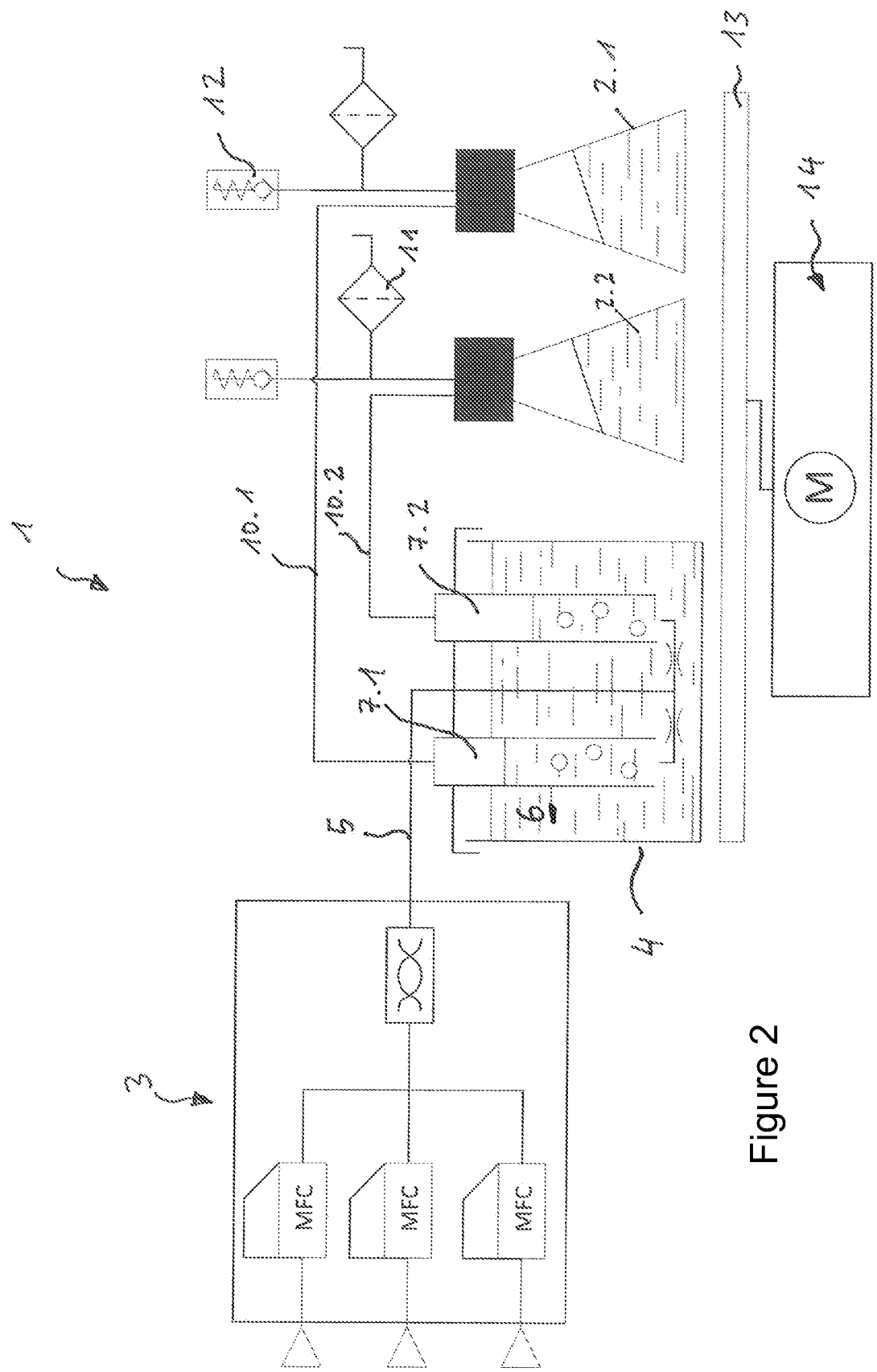
FIG. 2 shows a gas supply system according to FIG. 1 with shaken bioreactors.

FIG. 2 shows a gas supply system (1) corresponding to FIG. 1, which differs only in as much as the container (4) and the bioreactors (2.1, 2.2) are arranged not in a stationary fashion but instead on a platform (13) of a rotary shaker (14). The gas provision (3), however, is arranged, unchanged, in a stationary fashion. The feed line (5), therefore, up to the section which immerges into the liquid charge (6) and is implemented as a tube, must be of flexible implementation, in order to allow the shaking movement during supply of gas.

Figure 3:
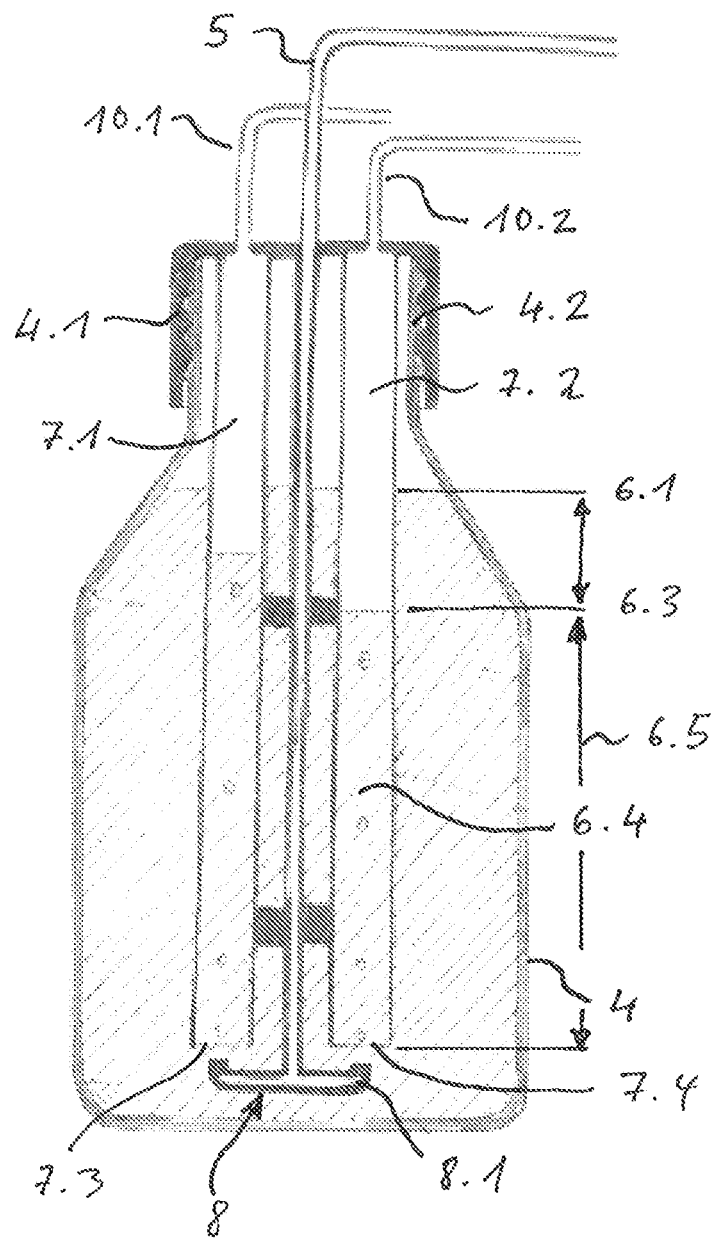
FIG. 3 shows an embodiment of a container for distributing and humidifying a gas stream.

FIG. 3 shows one possible embodiment of a container (4). The container (4) is designed as a bottle, with its upper opening (4.2) closable with a screw-action cover (4.1). From the figure it is apparent that the feed line (5) and the riser lines (7.1, 7.2) in the liquid charge (6) extend in the direction of a perpendicular to the liquid level (6.1). To compensate the shaking movement, the riser lines (7.1, 7.2) designed as tubes are mounted circularly around the feed line (5) on the cover (4.1). Directly with the screwing-on of the cover (4.1) on the container (4), all of the riser lines (7.1, 7.2), the section of the feed line (5) extending into the container (4), and the distributor (8) in fluid communication with the feed line (5) are correctly positioned within the container (4) and aligned with one another.

Figure 4:
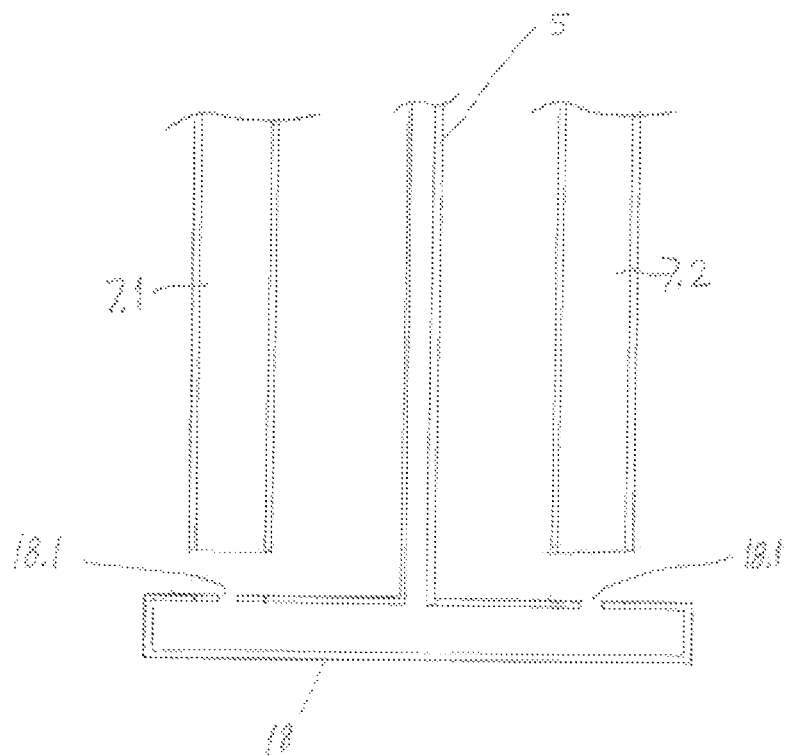
FIG. 4 shows an alternative embodiment of the distributor.

The distributor (8) has a plurality of distributor tubes (8.1) which extend outwardly in star shape from the feed line (5). Where six riser lines (7.1, 7.2) are arranged circularly around the feed line (5), the distributor (8) has six distributor tubes (8.1). Each distributor tube (8.1) opens out at the end in an exit opening of reduced diameter, which opens out below the lower opening (7.3, 7.4) of one of the riser lines (7.1, 7.2) within the liquid charge (6). In the exemplary embodiment shown, the exit openings are located just below the lower openings (7.3, 7.4). The radial extent of all the distributor tubes (8.1), the geometry of the outlet openings at the ends of the distributor tubes (8.1), and the position of the outlet openings with respect to the lower openings (7.3, 7.4) of the riser lines are consistent, and so consistent gas substreams enter from the distributor (8) under consistent conditions into the riser lines (7.1, 7.2). Instead of having distributor tubes, the distributor could alternatively be a hollow-cylindrical gas collector (18) in fluid communication with the feed line (5) with orifice plates (18.1) aligned with the lower openings of the riser lines (7.1, 7.2) as shown in FIG. 4.

| No. | Designation |
|---|---|
| 1. | Gas supply system |
| 2.1 | Bioreactor |
| 2.2 | Bioreactor |
| 3. | Gas provision |
| 3.1 | Gas sources |
| 3.2 | Entry |
| 3.3 | Exit |
| 3.4 | Mass flow controller |
| 3.5 | Mixing facility |
| 4. | Container |
| 4.1 | Cover |
| 4.2 | Opening |
| 5. | Feed line |
| 6. | Liquid charge |
| 6.1 | Liquid level |
| 6.3 | Liquid surface |
| 6.4 | Column of liquid |
| 6.5 | Height of the column of liquid |
| 7.1 | Riser lines |
| 7.2 | Riser lines |
| 7.3 | Lower opening |
| 7.4 | Lower opening |
| 7.5 | Upper opening |
| 7.6 | Upper opening |
| 8. | Distributor |
| 8.1 | Distributor tubes |
| 9.1 | Gas substream |
| 9.2 | Gas substream |
| 10.1 | Gas line |
| 10.2 | Gas line |
| 11. | Offgas filter |
| 12. | Pressure relief valve |
| 13. | Platform |
| 14. | Rotary shaker |

The invention claimed is:

1. A method for supplying gas to a plurality of bioreactors, comprising the steps of:
    providing a constant gas stream;
    feeding the constant gas stream into a container having a liquid charge;
    dividing the gas constant stream into a plurality of gas substreams;
    introducing each of the gas substreams into the liquid charge, wherein the gas substreams are introduced into lower openings of respective riser lines that are immerged into the liquid charge; and
    feeding the gas substreams to the interiors of respective ones of the bioreactors through gas lines gastightly connected to upper openings of the respective riser lines.

2. The method as claimed in claim 1, wherein each of the plurality of gas substreams has a consistent gas flow.

3. The method as claimed in claim 1, wherein the step of introducing includes releasing the gas substreams into the liquid charge at a consistent vertical distance to a liquid level of the liquid charge.

4. The method as claimed in claim 1, wherein the step of introducing includes introducing the gas substreams into the respective riser lines at a consistent vertical distance to a liquid level of the liquid charge.

5. The method as claimed in claim 1, further comprising the step of shaking the bioreactors and the container at least during the feeding of the gas substreams to the interiors of the respective bioreactors.

6. A gas supply system for supplying gas to a plurality of bioreactors, comprising:
    a gas provision with a feed line providing a gas stream having a constant flow into the feed line;
    a container having a liquid charge;
    a plurality of riser lines immerged in the liquid charge, each of the riser lines having a lower opening;
    a distributor in fluid communication with the feed line which divides the gas stream into a plurality of gas substreams and introduces the gas substreams into the liquid charge and respective ones of the riser lines; and
    a plurality of gas lines gastightly connected to upper openings of the riser lines, each of the gas lines being connectable for fluid communication with interiors of respective ones of the bioreactors.

7. The gas supply system as claimed in claim 6, wherein the gas provision includes a gas mixing system having entries connected to a plurality of gas sources and an exit connected to the feed line.

8. The gas supply system as claimed in claim 7, wherein the gas mixing system has a mass flow controller for each gas source.

9. The gas supply system as claimed in claim 6, further comprising a rotary shaker with a shaker platform for receiving the bioreactors and the container.

10. The gas supply system as claimed in claim 9, wherein the riser lines are tubes arranged circularly around a perpendicular line to a liquid level of the liquid charge.

11. The gas supply system as claimed in claim 10, wherein
    the perpendicular line and a longitudinal central axis of the feed line are coincident; and
    the distributor has a plurality of distributor tubes extending outwardly in a star shape from the feed line, with each distributor tube being in fluid communication with the feed line and having an outlet opening or a group of outlet openings, which open out below the lower opening or within one of the riser lines in the liquid charge.

12. The gas supply system as claimed in claim 10, wherein
    the perpendicular line and a longitudinal central axis of the feed line are coincident; and
    the distributor has a hollow-cylindrical gas collector, which is in fluid communication with the feed line, the hollow-cylindrical gas collector including an upper end face on which a plurality of orifice plates are arranged, each of the orifice plates opening out below the lower opening of a respective one of the riser lines.

13. The gas supply system as claimed in claim 12, wherein the longitudinal central axis of the feed line and a longitudinal axis of the gas collector are coincident, and all of the orifice plates are geometrically consistent and arranged at a consistent radial distance to the longitudinal central axis in the gas collector.

14. The gas supply system as claimed in claim 6, wherein the feed line and the riser lines in the liquid charge extend perpendicularly to a liquid level of the liquid charge.

15. The gas supply system as claimed in claim 14, wherein the container has a cover closing an opening, and the feed line and the riser lines are mounted on the cover as an assembly.

16. The gas supply system as claimed in claim 6, further comprising the bioreactors, wherein each of the bioreactors includes at least one of a pressure relief valve and an offgas filter.

17. The gas supply system as claimed in claim 6, wherein the container and the riser lines are made at least partially with transparent material.

* * * * *